US009333012B2

(12) United States Patent
Beale et al.

(10) Patent No.: US 9,333,012 B2
(45) Date of Patent: May 10, 2016

(54) SPINAL IMPLANT SYSTEM AND METHOD

(75) Inventors: Jeffrey W. Beale, Bartlett, TN (US);
Larry T. McBride, Memphis, TN (US);
Keith E. Miller, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 284 days.

(21) Appl. No.: 13/280,462

(22) Filed: Oct. 25, 2011

(65) Prior Publication Data
US 2013/0103094 A1 Apr. 25, 2013

(51) Int. Cl.
*A61B 17/70* (2006.01)

(52) U.S. Cl.
CPC ........... *A61B 17/7076* (2013.01); *A61B 17/708* (2013.01); *A61B 17/7082* (2013.01)

(58) Field of Classification Search
USPC ................ 606/86 A, 250–260, 261–279
See application file for complete search history.

(56) References Cited

U.S. PATENT DOCUMENTS

| 5,474,558 | A   |     | 12/1995 | Neubardt           |         |
|-----------|-----|-----|---------|--------------------|---------|
| 5,662,658 | A   |     | 9/1997  | Wenstrom, Jr.      |         |
| 6,183,472 | B1  | *   | 2/2001  | Lutz ............. | 606/86 A |
| 6,616,663 | B2  |     | 9/2003  | Glenn, III et al.  |         |
| 6,660,010 | B2  |     | 12/2003 | Gellman            |         |
| 6,755,836 | B1  |     | 6/2004  | Lewis              |         |
| 6,932,822 | B2  |     | 8/2005  | Oribe et al.       |         |
| 7,575,581 | B2  |     | 8/2009  | Lovell             |         |
| 7,686,835 | B2  |     | 3/2010  | Warnick            |         |
| 7,722,651 | B2  |     | 5/2010  | Kwak et al.        |         |
| 7,875,031 | B2  |     | 1/2011  | Chin et al.        |         |
| 7,909,834 | B2  |     | 3/2011  | Selover            |         |
| 7,918,858 | B2  |     | 4/2011  | Stad et al.        |         |
| 7,981,117 | B2  |     | 7/2011  | Newton et al.      |         |
| 7,988,694 | B2  | *   | 8/2011  | Barrus et al. ..... | 606/86 A |
| 7,988,699 | B2  |     | 8/2011  | Martz et al.       |         |
| 8,012,185 | B2  |     | 9/2011  | Warnick            |         |
| 8,066,739 | B2  | *   | 11/2011 | Jackson ........... | 606/246 |
| 8,092,458 | B2  | *   | 1/2012  | Geist et al. ..... | 606/86 A |
| 8,142,437 | B2  | *   | 3/2012  | McLean et al. .... | 606/86 A |
| 8,439,922 | B1  | *   | 5/2013  | Arnold et al. .... | 606/86 A |
| 8,439,924 | B1  | *   | 5/2013  | McBride et al. ... | 606/86 A |
| 2004/0138662 | A1 | * | 7/2004  | Landry et al. .... | 606/61 |
| 2004/0172022 | A1 | * | 9/2004  | Landry et al. .... | 606/61 |
| 2005/0131408 | A1 | * | 6/2005  | Sicvol et al. .... | 606/61 |
| 2005/0192579 | A1 | * | 9/2005  | Jackson ........... | 606/72 |
| 2005/0245928 | A1 | * | 11/2005 | Colleran et al. .. | 606/61 |

(Continued)

OTHER PUBLICATIONS

Synthes, Pangea Degenerative Spine System—Surgical Technique (Draft) pp. 1-30 2006, Synthes, Einmattstrasse 2, CH-4436 Oberdorf, Switzerland.

(Continued)

*Primary Examiner* — Jan Christopher Merene (57) ABSTRACT

A spinal implant system includes a first member including at least one wall, which includes a first axial end surface, a second axial end surface and an outer surface including a locking cavity. A second member includes a first extension defining an inner surface and a second extension defining an inner surface, the inner surfaces defining a first cavity therebetween. At least one of the inner surfaces includes a first angled portion and a second angled portion. A third member is disposed in the first cavity, and includes a first arm and a second arm, at least one of the arms includes a protrusion. The third member is configured for axial translation relative between a first orientation and a second orientation. Methods of use are disclosed.

20 Claims, 9 Drawing Sheets

(56) References Cited

U.S. PATENT DOCUMENTS

| | | |
|---|---|---|
| 2006/0247630 A1* | 11/2006 | Iott et al. .................... 606/61 |
| 2006/0247658 A1* | 11/2006 | Pond et al. .................. 606/104 |
| 2007/0233155 A1* | 10/2007 | Lovell ......................... 606/104 |
| 2008/0045970 A1 | 2/2008 | Saidha et al. |
| 2008/0119862 A1* | 5/2008 | Wicker et al. ................. 606/99 |
| 2008/0125817 A1* | 5/2008 | Arnett et al. ................ 606/319 |
| 2008/0161857 A1* | 7/2008 | Hestad et al. ............... 606/264 |
| 2008/0275456 A1* | 11/2008 | Vonwiller et al. ............. 606/99 |
| 2009/0042164 A1 | 2/2009 | Machata et al. |
| 2009/0054902 A1 | 2/2009 | Mickiewicz et al. |
| 2009/0082775 A1* | 3/2009 | Altarac et al. ................ 606/90 |
| 2009/0228053 A1* | 9/2009 | Kolb et al. .................. 606/86 A |
| 2009/0228054 A1* | 9/2009 | Hoffman et al. ............ 606/86 A |
| 2010/0082045 A1 | 4/2010 | Petersen et al. |
| 2010/0137875 A1 | 6/2010 | Marino et al. |
| 2010/0331897 A1 | 12/2010 | Lindner |
| 2011/0184473 A1 | 7/2011 | Garcia-Bengochea et al. |
| 2011/0313460 A1* | 12/2011 | McLean et al. ............. 606/264 |

OTHER PUBLICATIONS

Synthes, Pangea Degenerative Spine System—Technique Guide pp. 1-31 2006, Synthes Spine.

* cited by examiner

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, a spinal implant system is provided. The spinal implant system includes a first member having a proximal portion including at least one wall defining an implant cavity and a distal portion including a tissue penetrating portion. The wall including a first axial end surface, a second axial end surface and an outer surface extending therebetween. The outer surface includes a locking cavity. A second member extends between a proximal end and a distal end, and includes a first extension defining an inner surface and a second extension defining an inner surface, the inner surfaces defining a first cavity therebetween. At least one of the inner surfaces includes a first angled portion adjacent the distal end and a second angled portion adjacent the distal end. A third member is disposed in the first cavity, and includes a first arm and a second arm, at least one of the arms includes a protrusion. The third member is configured for axial translation relative to the second member between a first orientation such that the protrusion extends distal to the distal end of the second member to engage the locking cavity and a second orientation such that the protrusion is disposed within the locking cavity and the first angled portion engages the axial end surfaces and the second angled portion engages the arm.

In one embodiment, the spinal implant system comprises a bone fastener including a proximal portion having opposing wall portions defining a first implant cavity. Each wall portion includes a first axial end surface, a second axial end surface and an outer surface extending therebetween. The outer surface includes a transverse groove. A sleeve extends between a proximal end and a distal end, and includes a first extension having an inner surface defining a first angled portion adjacent the distal end and a second angled portion adjacent the distal end. The sleeve also includes a second extension including an inner surface defining a first angled portion adjacent the distal end and a second angled portion adjacent the distal end, the inner surfaces defining a first cavity therebetween. An extender is disposed in the first cavity, and includes a first arm having a transverse protrusion and a second arm having a transverse protrusion. The extender is configured for axial translation relative to the sleeve between a first orientation such that the transverse protrusions extend distal to the distal end of the sleeve to engage the transverse grooves and a second orientation such that the transverse protrusions are disposed within the transverse grooves and the first angled portions engage the axial end surfaces and the second angled portions engage the arms.

In one embodiment, a method for treating a spine is provided, which includes the steps of providing a spinal implant system having a first member with a proximal portion having at least one wall defining an implant cavity and a distal portion including a tissue penetrating portion, the walls include a first axial end surface, a second axial end surface and an outer surface extending therebetween, the outer surface includes a locking cavity, a second member extends between a proximal end and a distal end and includes a first extension defining an inner surface and a second extension defining an inner surface, the inner surfaces define a first cavity therebetween, at least one of the inner surfaces includes a first angled portion adjacent the distal end a second angled portion adjacent the distal end, a third member is disposed in the first cavity and includes a first arm and a second arm, at least one of the arms includes a protrusion; axially translating the third member relative to the second member to a first orientation such that the third member extends distal to the distal end of the second member; engaging the protrusion with the locking cavity in the first orientation; axially translating the third member relative to the second member to a second orientation such that the protrusion is disposed within the locking cavity and the first angled portion engages the axial end surfaces and the second angled portion engages the arm.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. It is envisioned that the surgical implant system can include a bone fastener having a head with a cut that allows the head to be captured and retained under tension and lateral compression. It is further envisioned that the tension may be applied through a member, such as, for example, an extender and that compression may be applied through another member, such as, for example, a sleeve.

It is envisioned that the system may include instruments that are connected or attached to an extender(s) such as, for example, a lateral translation handle or derotaton instruments. It is further envisioned that the system may have an extender with a quick release mechanism to allow the extender to slide into engagement with an implant. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present embodiments may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there is illustrated components of a surgical system, such as, for example, a spinal implant system in accordance with the principles of the present disclosure.

The components of the spinal implant system can be fabricated from biologically acceptable materials suitable for medical applications, including metals, synthetic polymers, ceramics and bone material and/or their composites, depending on the particular application and/or preference of a medical practitioner. For example, the components of the spinal implant system, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSa$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the spinal implant system may have material composites, including the above materials, to achieve various desired characteristics such as strength, rigidity, elasticity, compliance, biomechanical performance, durability and radiolucency or imaging preference. The components of the spinal implant system, individually or collectively, may also be fabricated from a heterogeneous material such as a combination of two or more of the above-described materials. The components of the spinal implant system may be monolithically formed, integrally connected or include fastening elements and/or instruments, as described herein.

The spinal implant system is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that the spinal implant system and method may be employed with treatments using minimally invasive and percutaneous techniques.

The spinal implant system includes a first member, such as, for example, a bone fastener 30, a second member, such as, for example, a sleeve 32 and a third member, such as, for example, an extender 34. Bone fastener 30 includes a proximal portion 31 configured to receive and couple a spinal construct, such as vertebral rod, for example. Proximal portion 31 includes opposing wall portions 36, 38 each having an arcuate shape and defining a first implant cavity 40. In one embodiment, first implant cavity 40 is generally U-shaped and is configured to receive a cylindrical spinal construct, such as, for example, a vertebral rod. It is contemplated that the cross-section of the vertebral rod may have various configurations, for example, round, oval, rectangular, polygonal, irregular, tapered, offset, staggered, uniform and non-uniform. It is envisioned that first implant cavity 40 may have other configurations, including, for example, V-shaped, polygonal, or tapered depending upon the geometry of the spinal construct to be received within first implant cavity 40.

Figure 1:
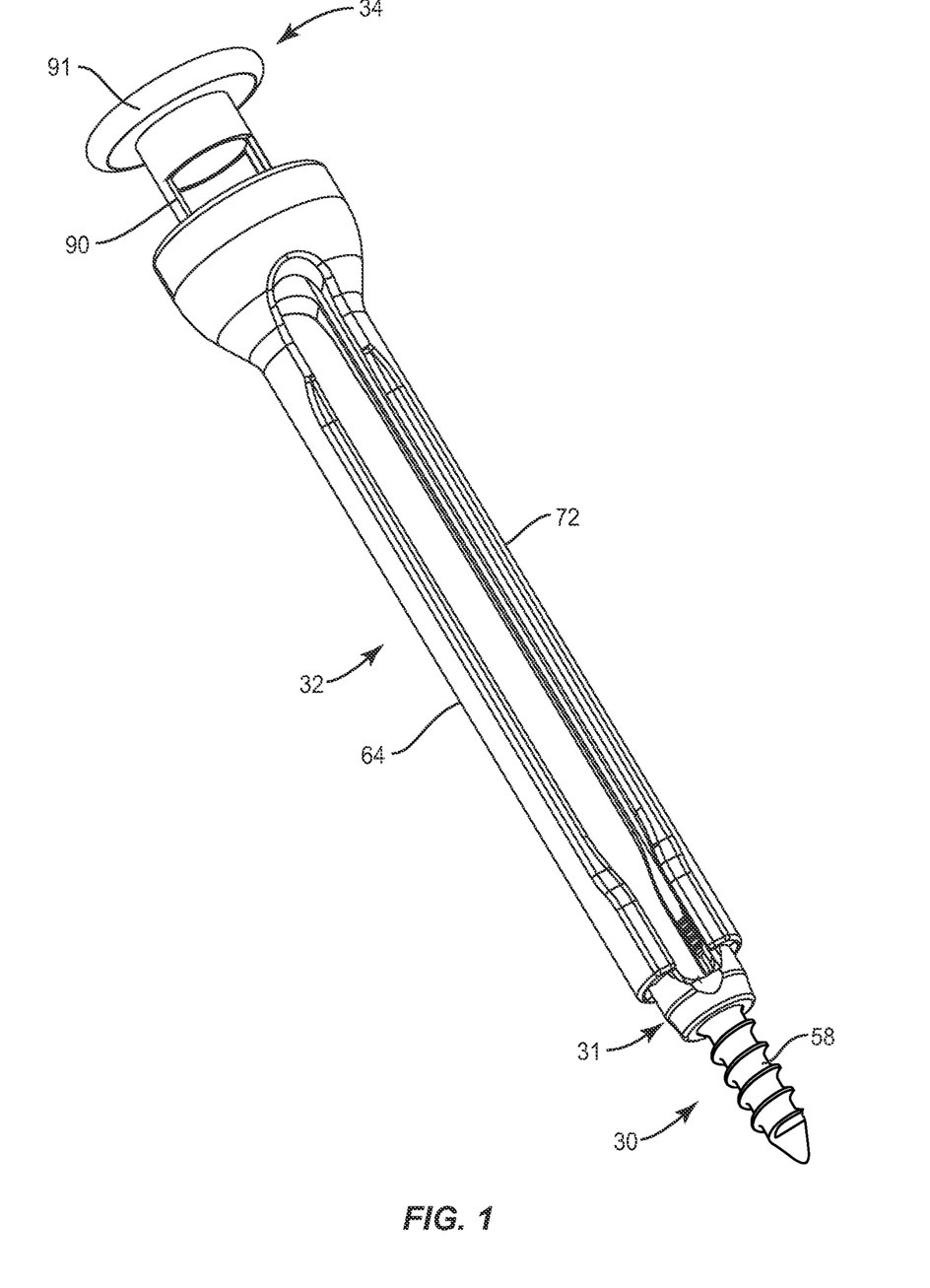
FIG. 1 is a perspective view of one particular embodiment of the system in accordance with the principles of the present disclosure.
Figure 2:
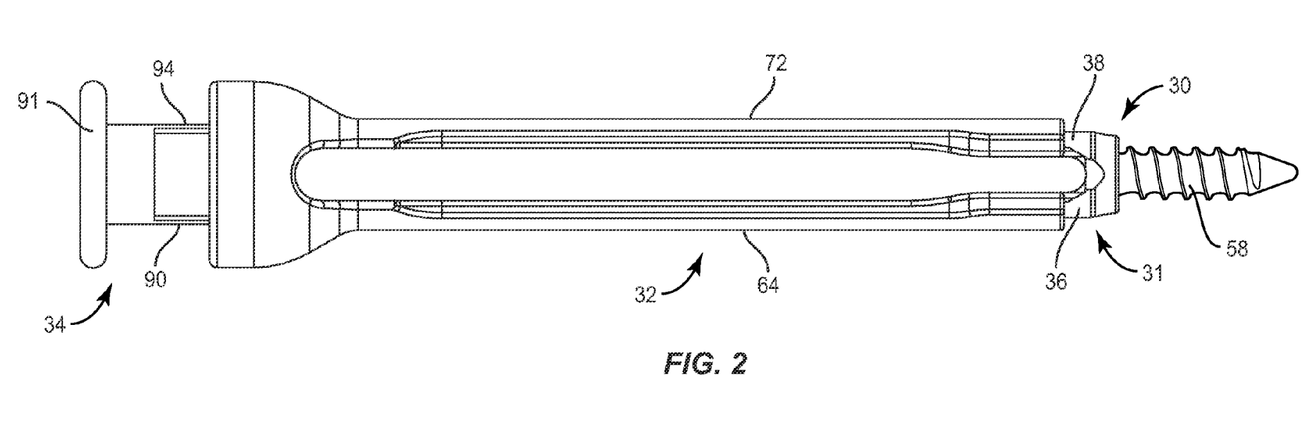
FIG. 2 is a side view of the system shown in FIG. 1.
Figure 3:
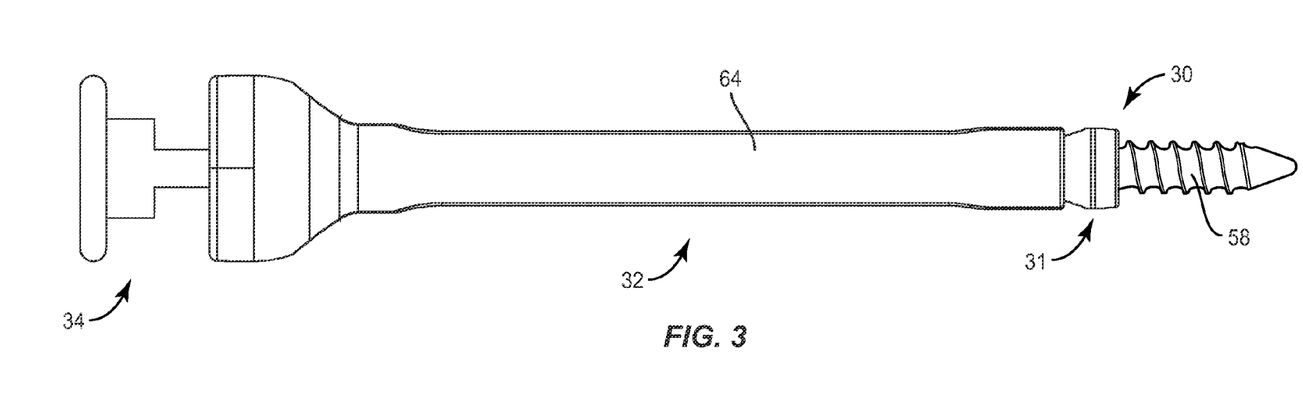
FIG. 3 is a side view of the system shown in FIG. 1.
Figure 4:
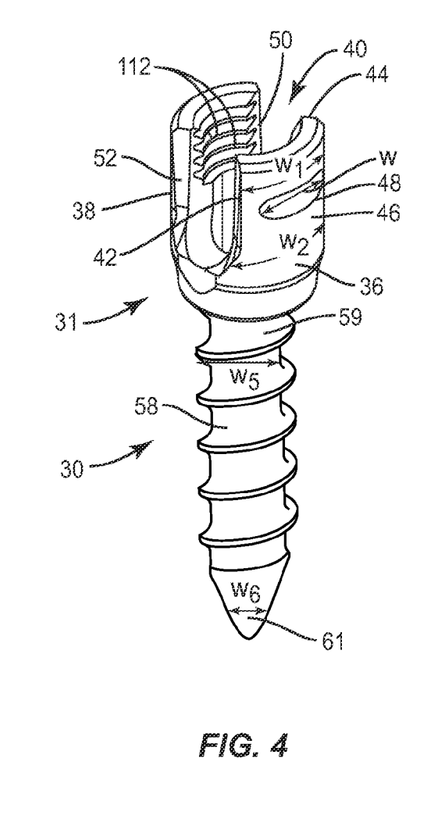
FIG. 4 is a perspective view of a first member of the system shown in FIG. 1.
Figure 5:
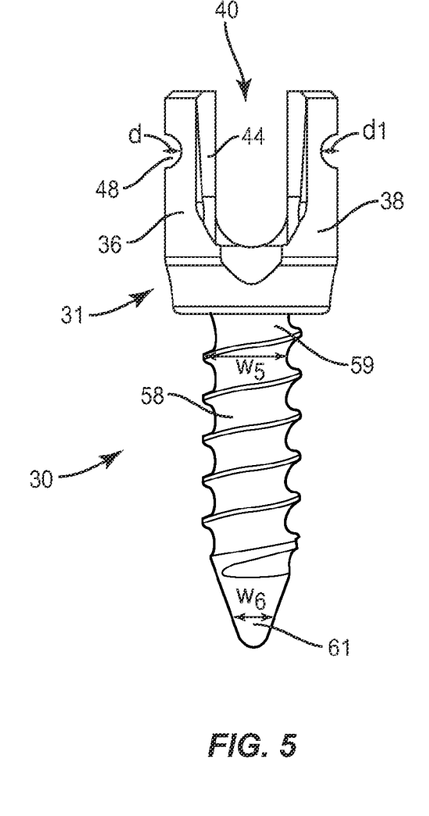
FIG. 5 is a side view of the first member shown in FIG. 4.
Figure 6:
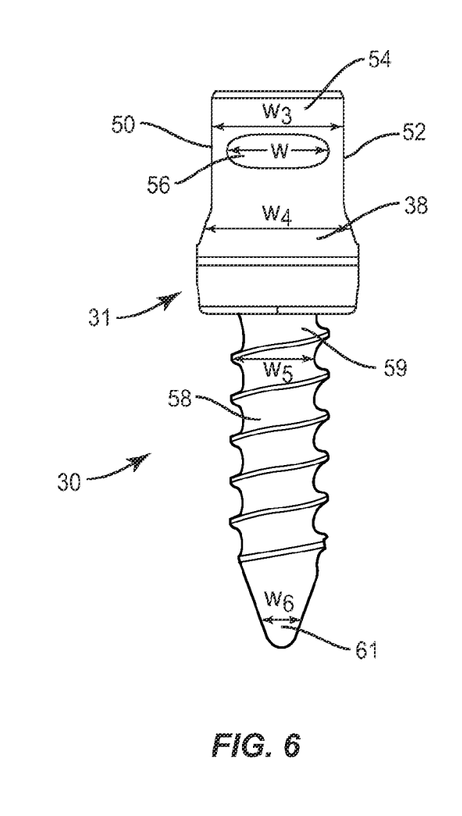
FIG. 6 is a side view of the first member shown in FIG. 4.

Wall portion 36 extends between a proximal end having a width $w_1$ and a distal end having a width $w_2$. Wall portion 38 extends between a proximal end having a width $w_3$ and a distal end having a width $w_4$. In one embodiment, wall portion 36 is tapered between the proximal and distal ends thereof such that width $w_2$ is greater than width $w_1$ and wall portion 38 is tapered between the proximal and distal ends thereof such that width $w_4$ is greater than width $w_3$. Wall portions 36, 38 are configured for engagement with a first angled portion of sleeve 32, as will be discussed. It is contemplated that the amount of taper of wall portions 36, 38 depends on the geometry of the first angled portion of sleeve 32 which receive wall portions 36, 38. It is further contemplated that the taper of bone fastener 30 is configured to wedge one or both of the wall portions of bone fastener 30 with sleeve 32. It is envisioned that wall portions 36, 38 may have uniformly increasing or decreasing taper, arcuate, staggered and/or offset portions. In one embodiment, wall portions 36, 38 have substantially linear axial end surfaces such that wall portions 36, 38 are non-tapered and, width $w_1$ is substantially equal to width $w_2$ and/or width $w_4$ is substantially equal to width $w_3$.

Wall portion 36 includes a first axial end surface 42, a second axial end surface 44 and an outer surface 46 extending therebetween, which includes a locking cavity, such as, for example, a groove 48 oriented transverse relative to a longitudinal axis defined by bone fastener 30. Transverse groove 48 is formed with outer surface 46 such that transverse groove 48 has a depth d. Wall portion 38 includes a first axial end surface 50, a second axial end surface 52 and an outer surface 54 extending therebetween, which includes a locking cavity, such as, for example, a groove 56 oriented transverse relative to a longitudinal axis defined by bone fastener 30. Transverse groove 56 is formed with outer surface 54 such that transverse groove 56 has a depth d1. It is contemplated that grooves 48, 56 allow bone fastener 30 to be captured and retained under tension and lateral compression by the extender. It is envisioned that one or all of the surfaces of wall portions 36, 38 have alternate surface configurations, such as, for example, rough, threaded for connection with surgical instruments, arcuate, undulating, porous, semi-porous, dimpled, polished and/or textured according to the requirements of a particular application.

First and second axial end surfaces 42, 44 are configured to engage with a first extension of sleeve 32 and first and second axial end surfaces 50, 52 are configured to engage with a second extension of sleeve 32 such that at least a portion of walls 36, 38 are received within sleeve 32, as will be discussed. Axial end surfaces 42, 44, 50, 52 have an angled orientation relative to the outer circumference or perimeter defined by outer surfaces 46, 54, which engage angled surfaces of the first and second extensions of sleeve 32. It is envisioned that the angled surfaces are oriented as cephalad/caudal surfaces of bone fastener 30 to facilitate fixation with sleeve 32 and resist medial/lateral deflection of the components of the spinal implant system, such as, sleeve 32 and extender 34. It is further envisioned that one or all of end surfaces 42, 44, 50, 52 may be disposed in an orientation relative to the outer circumference or perimeter defined by outer surfaces 46, 54, and/or to other end surfaces, for example, perpendicular and/or selected angular orientations such as acute or obtuse, perpendicular and/or parallel.

Transverse grooves 48, 56 are configured to receive protrusions on the distal end of extender 34. It is contemplated that the depth of transverse grooves 48, 56 corresponds to the depth of the protrusions on the distal end of extender 34, which are received within transverse grooves 48, 56. Transverse groove 48 has a width w, which is less than widths $w_1$, $w_2$ of wall portion 36 and transverse groove 56 has a width w which is less than widths $w_3$ and $w_4$ of wall portion 38. In one embodiment, transverse groove 48 extends between first and second axial end surfaces 42, 44 without extending through first and second axial end surfaces 42, 44, and transverse groove 56 extends between first and second axial end surfaces 50, 52 without extending through first and second axial end surfaces 50, 52. It is envisioned that transverse groove 48 may extend through first and second axial end surfaces 42, 44 and that transverse groove 56 may extend through first and second axial end surfaces 50, 52 by increasing the depths d of transverse grooves 48, 56. In one embodiment, transverse grooves 48, 56 have a generally U-shaped cross-section. It is envisioned that transverse grooves 48, 56 may have other cross-sectional configurations, including, for example, flat bottomed channel, a cut similar to a rack and pinion, V-shaped, W-shaped, polygonal, tapered or a configuration configured to accept a gear tooth. It is further envisioned that one or both of grooves 48, 56 may be transversely oriented relative to a longitudinal axis of bone fastener 30, such as, for example, perpendicular, angled, and/or may be disposed in parallel orientation relative to a longitudinal axis of bone fastener 30. In one embodiment, the locking cavity of wall portion 36 and/or wall portion 38 includes a recess. It is envisioned that the recess may include a blind hole. It is further envisioned that the recess may formed a greater depth within the surface of wall portion 36 and/or wall portion 38 without extruding through the respective axial end surfaces. In one embodiment, wall portion 36 and/or wall portion 38 can include multiple locking cavities, such as, for example, multiple recesses or multiple transverse grooves, which may have shapes and orientations, similar to those alternatives described herein. For example, wall portion 36 and/or wall portion 38 can include at least two transverse grooves such that a first transverse groove is disposed above a second transverse groove, or such that a first locking cavity and a second locking cavity are smaller in length and disposed in a side by side arrangement. It is envisioned that the arm(s) of extender 34 include corresponding multiple protrusions for engagement with the multiple locking cavities.

In one embodiment, the inner surfaces of wall portions 36, 38 include internal threads 112. Internal threads 112 may be configured to receive a set screw to fix the position of a vertebral construct, such as a vertebral rod, for example, within implant cavity 40 of bone fastener 30. It is envisioned that internal threads 112 may be reverse angle threads such that threads 112 may include a forward face that points down and in toward implant cavity 40.

Bone fastener 30 includes a distal portion having a tissue penetration portion 58 configured to attach to bone, such as, for example, one or more vertebrae during surgical treatment of a spinal disorder. Tissue penetrating portion 58 extends between a proximal end 59 and a distal end 61, and tapers from a first width $w_5$ at proximal end 59 to a second, reduced width $w_6$ at distal end 61. Proximal portion 31 of bone fastener 30 includes a bore configured to receive proximal end 59 of tissue penetrating portion 58 to couple tissue penetrating portion 58 to proximal portion 31. Tissue penetrating portion 58 is longitudinally aligned with proximal portion 31. In one embodiment, tissue penetrating portion 58 is rotationally fixed to proximal portion 31 so as to rotate around one or more axis such that tissue penetrating portion 58 is capable of multi-axial positioning with respect to proximal portion 31 of bone fastener 30. It is contemplated that tissue penetrating portion 58 or portions thereof can have various dimensions, for example, with regard to length, width, diameter, and thickness. It is further contemplated that the cross-sectional geometry of the various components of the spinal implant system may have various configurations including, for example, round, oval, rectangular, irregular, consistent, variable, uniform, and non-uniform.

As shown in FIGS. 7-10, sleeve 32 extends between a proximal end 60 and a distal end 62. Sleeve 32 includes a first extension 64 having an inner surface 66. Inner surface 66 defines a first angled portion 68 and a second angled portion 70 adjacent distal end 62. First angled portion 68 includes opposing faces 69, 71, which define a channel 73 therebetween disposed in a transverse orientation relative to a longitudinal axis of sleeve 32. Wall portion 36 of bone fastener 30 is received within transverse channel 73 such that first and second axial end surfaces 42, 44 engage faces 69, 71 for capture and retention of bone fastener 30 with sleeve 32. It is contemplated that faces 69, 71 are configured to mate with first and second axial end surfaces 42, 44 to facilitate such capture and retention and prevent wall portion 36 from moving within transverse channel 73. For example, this mating engagement can prevent bone fastener 30 from rotating within transverse channel 73. It is envisioned that one or both of faces 69, 71 may be disposed in an orientation relative to the inner surface circumference defined by channel 73, for example, perpendicular and/or selected angular orientations such as acute or obtuse, perpendicular and/or parallel. It is further envisioned that one or all of the surfaces of first extension 64 may have alternate surface configurations, such as, for example, rough, threaded for connection with surgical instruments, arcuate, undulating, porous, semi-porous, dimpled, polished and/or textured according to the requirements of a particular application. It is further envisioned that channel 73 may be transversely oriented relative to a longitudinal axis of sleeve 32, such as, for example, perpendicular, angled, and/or may be disposed in parallel orientation relative to a longitudinal axis of sleeve 32.

Sleeve 32 includes a second extension 72 including an inner surface 74. Inner surface 74 defines a first angled portion 76 and a second angled portion 78 adjacent distal end 62. First angled portion 76 includes opposing faces 77, 79, which define a channel 81 therebetween disposed in a transverse orientation relative to a longitudinal axis of sleeve 32. Wall portion 38 of bone fastener 30 is received within transverse channel 81 such that first and second axial end surfaces 50, 52 engage faces 77, 79 for capture and retention of bone fastener 30 with sleeve 32. It is contemplated that faces 77, 79 are configured to mate with first and second axial end surfaces 50, 52 to facilitate such capture and retention and prevent wall portion 36 from moving within transverse channel 81. For example, this mating engagement can prevent bone fastener 30 from rotating within transverse channel 81. It is envisioned that one or both of faces 77, 79 may be disposed in an orientation relative to the inner surface circumference defined by channel 81, for example, perpendicular and/or selected angular orientations such as acute or obtuse, perpendicular and/or parallel. It is further envisioned that one or all of the surfaces of second extension 72 may have alternate surface configurations, such as, for example, rough, threaded for connection with surgical instruments, arcuate, undulating, porous, semi-porous, dimpled, polished and/or textured according to the requirements of a particular application. It is further envisioned that channel 81 may be transversely oriented relative to a longitudinal axis of sleeve 32, such as, for example, perpendicular, angled, and/or may be disposed in parallel orientation relative to a longitudinal axis of sleeve 32.

End surfaces 42, 44 are configured for capture by faces 69, 71 and end surfaces 50, 52 are configured for capture by faces 77, 79. Faces 69, 71 of transverse channel 73 are substantially linear and configured for engagement with the tapered configuration of wall portion 36 such that at least a portion of the proximal end of wall portion 36 may be received within transverse channel 73 in a frictional engagement for capture and retention thereof. Faces 77, 79 of transverse channel 81 are substantially linear and configured for engagement with the tapered configuration of wall portion 38 such that at least a portion of the proximal end of wall portion 38 may be received within transverse channel 81 in a frictional engagement for capture and retention thereof. Each of transverse channels 73, 81 include a proximal stop configured to engage a proximal face of bone fastener 30. In one embodiment, end surfaces 42, 44 and/or end surfaces 50, 52 have a substantially linear configuration, discussed above, for capture by faces 69, 71 and/or faces 77, 79 respectively, which may or may not include frictional engagement.

Figure 9:
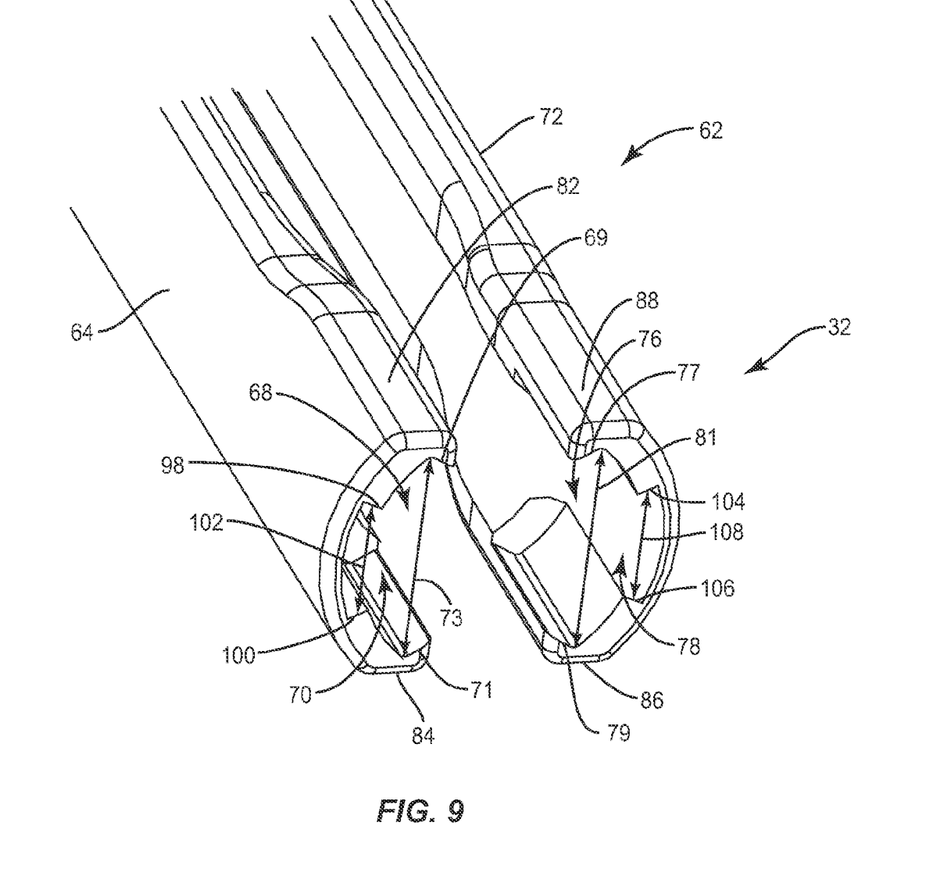
FIG. 9 is an enlarged break away perspective view of a distal end of the second member shown in FIG. 7.
Figure 10:
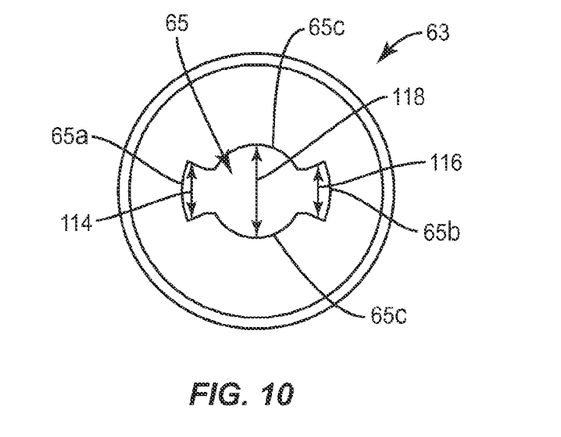
FIG. 10 is a top view of the second member shown in FIG. 7.

Second angled portion 70 includes opposing faces 98, 100 defining a longitudinal channel 102 disposed therebetween configured to receive a first arm of extender 34. It is envisioned that one or both of faces 98, 100 may be disposed in an orientation relative to the inner surface circumference defined by channel 102, for example, perpendicular and/or selected angular orientations such as acute or obtuse, perpendicular and/or parallel. Faces 98, 100 capture the first arm of extender 34 such that the first arm slidably engages faces 98, 100 to maintain the first arm within longitudinal channel 102 and facilitate relative axial translation of the first arm relative to sleeve 32.

Second angled portion 78 includes opposing faces 104, 106 defining a longitudinal channel 108 disposed therebetween configured to receive a second arm of extender 34. It is envisioned that one or both of faces 104, 106 may be disposed in an orientation relative to the inner surface circumference defined by channel 108, for example, perpendicular and/or selected angular orientations such as acute or obtuse, perpendicular and/or parallel. Faces 104, 106 capture the second arm of extender 34 such that the second arm slidably engages faces 104, 106 to maintain the second arm within longitudinal channel 108 and facilitate relative axial translation of the second arm relative to sleeve 32. Longitudinal channels 102, 108 extend in parallel between proximal end 60 and distal end 62 of extender 32. It is envisioned that one or both of channels 102, 108 may be disposed in an alternate orientation relative to sleeve 32, for example, at a selected angular orientations.

First and second extensions 64, 72 are integrally connected at proximal end 60 of sleeve 32. Inner surfaces 66, 74 of first and second extensions 64, 72 define a first cavity 80 therebetween. Sleeve 32 is engageable with bone fastener 30 such that first cavity 80 communicates with and is aligned with implant cavity 40 for disposal and relative movement of a vertebral construct, such as, for example, a vertebral rod, within first cavity 80 and implant cavity 40. Extensions 64, 72 define lateral openings 80a and 80b in communication with cavity 80. Openings 80a, 80b have a reduced thickness adjacent distal end 62. It is contemplated that openings 80a, 80b provide an opening that allows for an increased amount of rod reduction capabilities. It is further contemplated that the wall width of extensions 64, 72 provide a minimum cephalad/caudal width.

Figure 7:
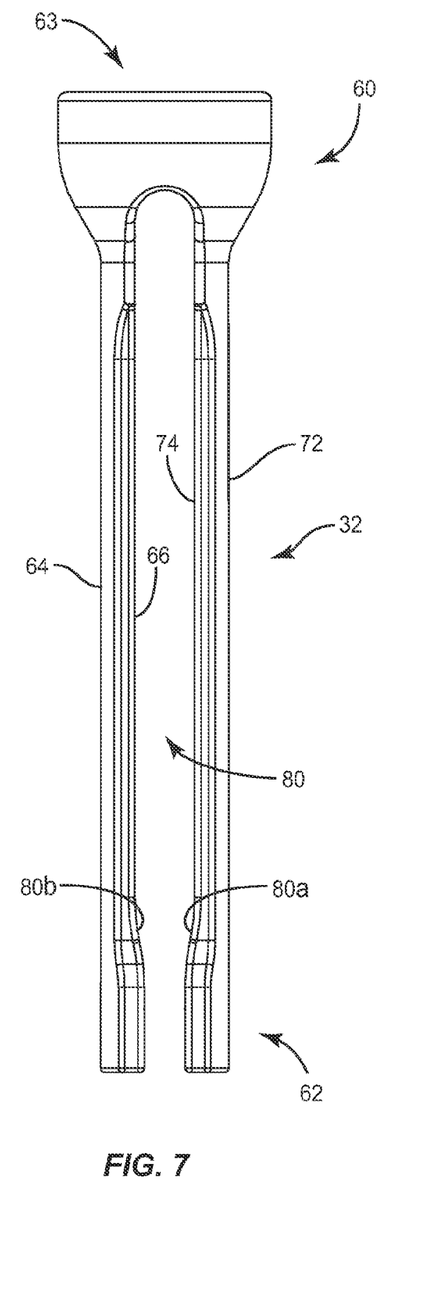
FIG. 7 is a side view of a second member of the system shown in FIG. 1.
Figure 8:
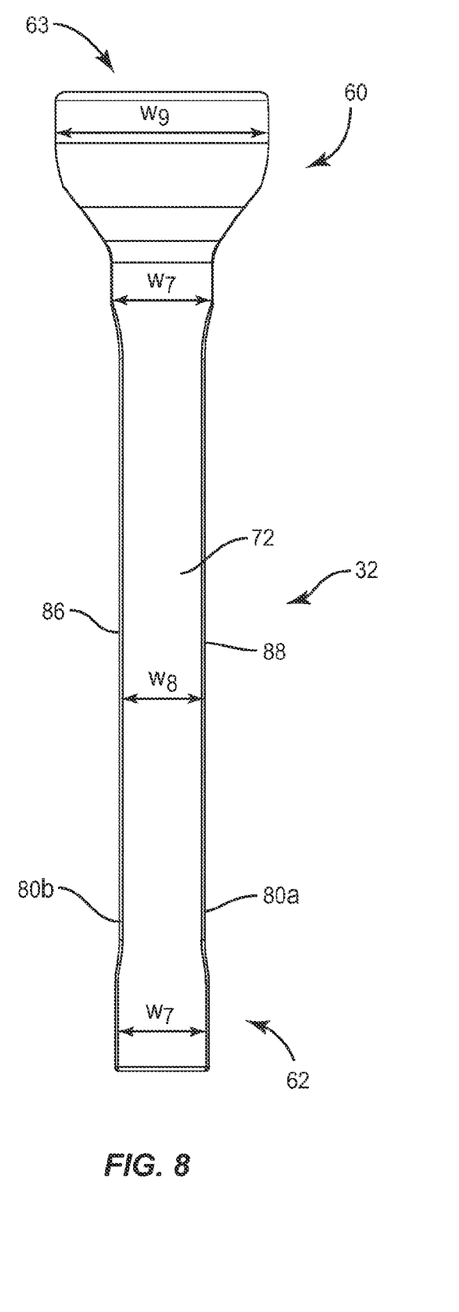
FIG. 8 is a side view of the second member shown in FIG. 7.

First and second extensions 64, 72 each include an outer surface, which is substantially uniform and even. The outer surfaces of first and second extensions 64, 72 have an arcuate surface configuration with a substantially crescent shaped cross section. First and second extensions 64, 72 are disposed in a parallel orientation. First extension 64 includes side surfaces 82, 84 and second extension 72 includes side surfaces 86, 88 such that first and second extension 64, 72 each have a first width $w_7$ at distal end 62 and/or proximal end 60 of sleeve 32 and a second, reduced width $w_8$ at a point midway between distal end 62 and proximal end 60. Proximal end 60 has a width $w_9$ which is greater than width $w_8$ of first and second extensions 64, 72 and tapers between a top portion 63 of proximal end 60 and first and second extensions 64, 72. In one embodiment, extensions 64, 72 extend from proximal end 60 in a cantilevered configuration, which may include a flexible, semi-rigid and/or rigid orientation.

Proximal end 60 includes a proximal face 63 having a keyway 65 formed therein sized and shaped to provide access for extender 34. Keyway 65 communicates with first cavity 80 to define a pathway for axial translation of extender 34 relative to sleeve 32. Keyway 65 extends between arcuate side surfaces 65a, 65b and includes concave upper and lower surfaces 65c extending between side surfaces 65a, 65b. Side surfaces 65a, 65b define arcuate channels 114, 116 configured to receive the arms of extender 34 and upper and lower surfaces 65c define a channel 118 configured to receive a proximal end of extender 34, as will be discussed. Arcuate channel 114 is in communication with longitudinal channel 102 and arcuate channel 116 is in communication with longitudinal channel 108.

Figure 11:
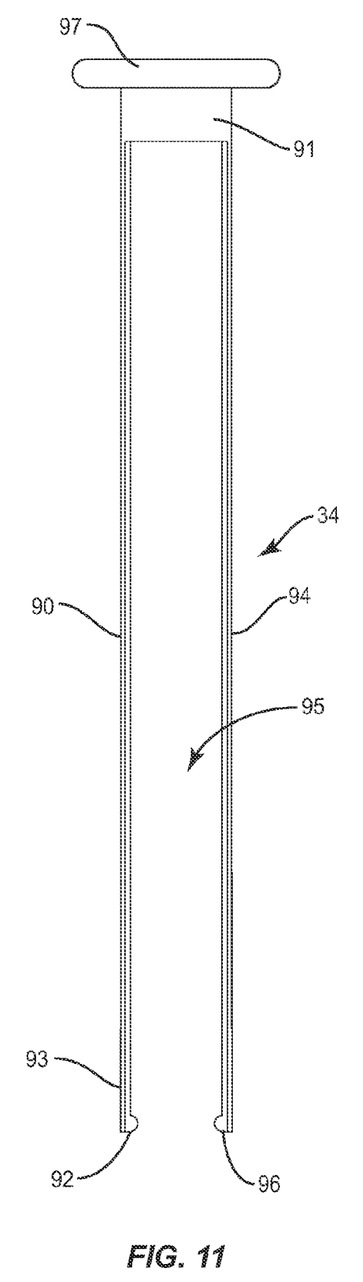
FIG. 11 is a side view of a third member of the system shown in FIG. 1.
Figure 12:
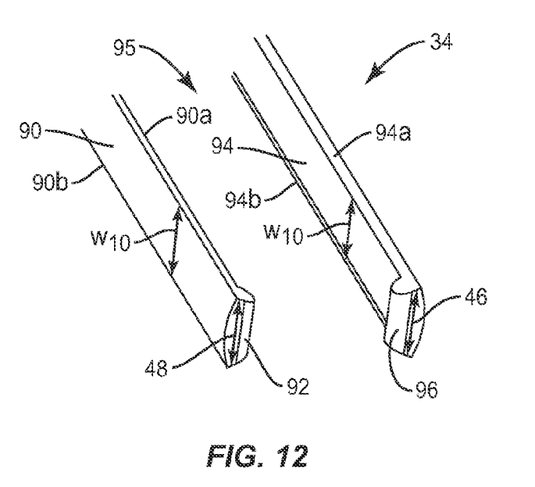
FIG. 12 is an enlarged break away perspective view of a distal end of the third member shown in FIG. 11.
Figure 13:
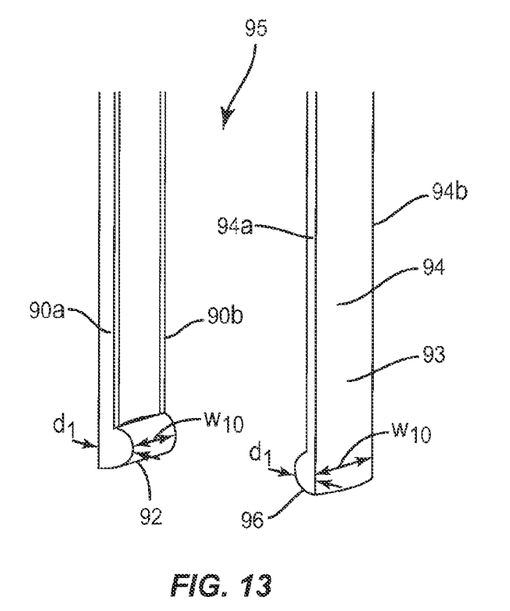
FIG. 13 is an enlarged break away perspective view of the third member shown in FIG. 11.

Extender 34 extends longitudinally between a proximal end 91 and a distal end 93 and is configured for disposal in first cavity 80. As shown in FIGS. 11-13, extender 34 includes a first arm 90, which includes a protrusion 92 oriented transverse relative to a longitudinal axis defined by extender 34. Extender 34 includes a second arm 94, which includes a protrusion 96 oriented transverse relative to a longitudinal axis defined by extender 34. It is envisioned that one or both of protrusions 92, 96 may be transversely oriented relative to a longitudinal axis of extender 34, such as, for example, perpendicular, angled, and/or may be disposed in parallel orientation relative to a longitudinal axis of extender 34.

First and second arms 90, 94 are integrally connected at proximal end 91. It is envisioned that first and second arms 90, 94 may be separately attachable and connected via clips, clamps, pins and/or an adhesive. Extender 34 is configured for axial translation relative to sleeve 32 between a first orientation and a second orientation. In the first orientation, transverse protrusions 92, 96 extend distal to distal end 62 of sleeve 32 to engage and/or disengage transverse grooves 48, 56 of bone fastener 30. In the second orientation, at least a portion of bone fastener 30 retracts within distal end 62 of sleeve 32 such that first angled portions 68, 76 engage axial end surfaces 42, 44, 50, 52. In the second orientation, bone fastener 30 is locked in position with extender 34 and sleeve 32. In one embodiment, arms 90, 94 extend from proximal end 91 in a cantilevered configuration, which may include a flexible, semi-rigid and/or rigid orientation. First and second arms 90, 94 of extender 34 define a channel 95 therebetween configured for disposal of a vertebral construct, such as a vertebral rod.

In one embodiment, proximal end 91 of extender 34 includes a proximal face 97 that defines an access opening (not shown). The opening is centrally disposed with proximal face 97 and can be aligned with keyway 65 upon assembly of the components of the spinal implant system. The opening and/or keyway 65 are disposed in a configuration to facilitate access of surgical instruments such as, for example, drivers and reducers, implants, biocompatible materials and/or biologically active agents, such as therapeutics and/or bone graft, adjacent bone fastener 30. For example, a setscrew can be passed through the opening and/or keyway 65 for delivery through extender 34 and/or sleeve 32 into bone fastener 30.

In one embodiment, extender 34 is biased to the second orientation. It is envisioned that transverse protrusions 92, 96 may be radially flexible to facilitate connection to and removal from transverse grooves 48, 56. It is further envisioned that transverse protrusions 92, 96 may be resilient such that transverse protrusions 92, 96 maintain tensile force applied to bone fastener 30 to maintain transverse protrusions 92, 96 within transverse grooves 48, 56.

Transverse protrusions 92, 96 each have a tapered width $w_{10}$ for disposal within transverse grooves 48, 56. Transverse protrusions 92, 96 extend from first and second arms 90, 94 a distance $d_1$ corresponding to depth d of transverse grooves 48, 56 such that transverse protrusions 92, 96 occupy substantially all of transverse grooves 48, 56 when transverse protrusions 92, 96 are received within transverse grooves 48, 56. Protrusions 92, 96 are fixed with grooves 48, 56 to retain and capture bone fastener 30 with extender 34 for axial translation of fastener 30 and extender 34 relative to sleeve 32, as described herein. It is envisioned that the configuration of the engagement of grooves and protrusions maintains tensile force applied to the head of bone fastener 30 for retention and capture.

First arm 90 extends between side surfaces such as, for example, first axial surface 90*a* and second axial surface 90*b*. Second arm 94 extends between side surfaces, such as, for example, first axial surface 94*a* and second axial surface 94*b*. First and second axial surfaces 90*a*, 90*b* of first arm 90 are angled such that first and second axial surfaces 90*a*, 90*b* correspond to the angle of faces 98, 100 of second angled portion 70 to facilitate disposal of first arm 90 within longitudinal channel 102. First and second axial surfaces 94*a*, 94*b* of second arm 94 are angled such that first and second axial surfaces 94*a*, 94*b* correspond to the angle of faces 104, 106 to facilitate disposal of second arm 94 within longitudinal channel 108. The axial surfaces of arms 90, 94 are captured within longitudinal channels 102, 108 to facilitate relative axial translation of arms 90, 94 relative to sleeve 32, as described.

In one embodiment, an actuator is disposed between and/or connected with sleeve 32 and/or extender 34. The actuator is engageable to dispose extender 34 in the first orientation and includes a biasing member to bias extender 34 to the second orientation. The biasing member may include a spring, for example, positioned between proximal end 60 of sleeve 32 and proximal end 91 of extender 34 when extender 34 is received within sleeve 32. When the spring is expanded, the distal ends of first and second arms 90, 94 of extender 34, including transverse protrusions 92, 96, are disposed within first cavity 80 of sleeve 32. First and second arms 90, 94 are received within longitudinal channels 102, 108 for axial translation therein. Advancing proximal end 91 of extender 34 distally causes the spring to compress and allows the distal ends of first and second arms 90, 94, including transverse protrusions 92, 96 to extend through distal end 62 of sleeve 32. Extender 34 engages bone fastener 30 such that transverse protrusions 92, 96 of extender 34 are disposed within transverse grooves 48, 56 of bone fastener 30.

Releasing proximal end 91 of extender 34 allows the spring to expand such that extender 34 axially translates proximally causing at least a portion of proximal portion 31 of bone fastener 30 to advance proximally into transverse channels 73, 81. Thus, releasing the spring causes extender 34 to retract such that at least a portion of bone fastener 30 is received within distal end 62 of sleeve 32. Bone fastener 30 engages sleeve 32 such that at least a portion of wall portion 36 is received within transverse channel 73 such that first and second axial end surfaces 42, 44 of wall portion 36 frictionally engage faces 69, 71 to prevent wall portion 36 from moving within transverse channel 73. At least a portion of wall portion 38 is received within transverse channel 81 such that first and second axial end surfaces 50, 52 of wall portion 38 frictionally engage faces 77, 79 to prevent wall portion 38 from moving within transverse channel 81.

In one embodiment, the spinal implant system includes a lock that prevents axial translation of extender 34 relative to sleeve 32. First and second arms 90, 94 of extender 34 may each include a first locking part, such as, for example, a protrusion extending from an outer surface of first and second arms 90, 94. In one embodiment, the protrusions extend from the outer surface of first and second arms 90, 94 at the distal ends thereof. It is envisioned that the protrusions may extend from the outer surface of first and second arms 90, 94 at the proximal ends thereof, or at any point between the proximal and distal ends of first and second arms 90, 94. The protrusions are configured for fixation with a second locking part of sleeve 32. In one embodiment, the protrusions have a shape that is round or oval. It is envisioned that the protrusions can be variously configured with regard to size and shape, and the shape may be rectangular, triangular, polygonal, and hexagonal, for example. It is also envisioned that first and second arms 90, 94 may include alternate locking or fastening parts to prevent axial translation of extender 34 relative to sleeve 32 such as, integral connection, threaded engagement, clips, friction fit, interference fit, pins, and/or adhesive.

In one embodiment, the inner surfaces of first and second extensions 64, 72 of sleeve 32 may each include a cavity defining a second locking part, such as, for example, an opening configured for fixation with the protrusions extending from the outer surfaces of first and second arms 90, 94. The openings are configured to receive the protrusions extending from the outer surfaces of first and second arms 90, 94. In one embodiment, the openings are oval or round. It is envisioned that the openings can be variously configured with regard to size and shape, and may have a shape which is rectangular, triangular, hexagonal, or any other shape that corresponds to the shape of the protrusions extending from the outer surfaces of first and second arms 90, 94 such that the protrusions may be received within the openings. The openings may extend through the inner surfaces of first and second extensions 64, 72.

In assembly, operation and use, the spinal implant system is employed with a surgical procedure for treatment of a spinal disorder affecting a section of a spine of a patient, as discussed herein. For example, the spinal implant system can be used with a surgical procedure for treatment of a condition or injury of an affected section of the spine including vertebrae.

In use, to treat the affected section of the spine, a medical practitioner obtains access to a surgical site including vertebrae in any appropriate manner, such as through incision and retraction of tissues. It is envisioned that the spinal implant system may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. The spinal implant system is then employed to augment the surgical treatment. The spinal implant system can be delivered or implanted as a pre-assembled device or can be assembled in situ. The spinal implant system may be completely or partially revised, removed or replaced, for example, removing bone fastener 30, sleeve 32 and/or extender 34, a vertebral rod and/or one or all of the components of the spinal implant system during or after the surgical procedure.

Figure 14:
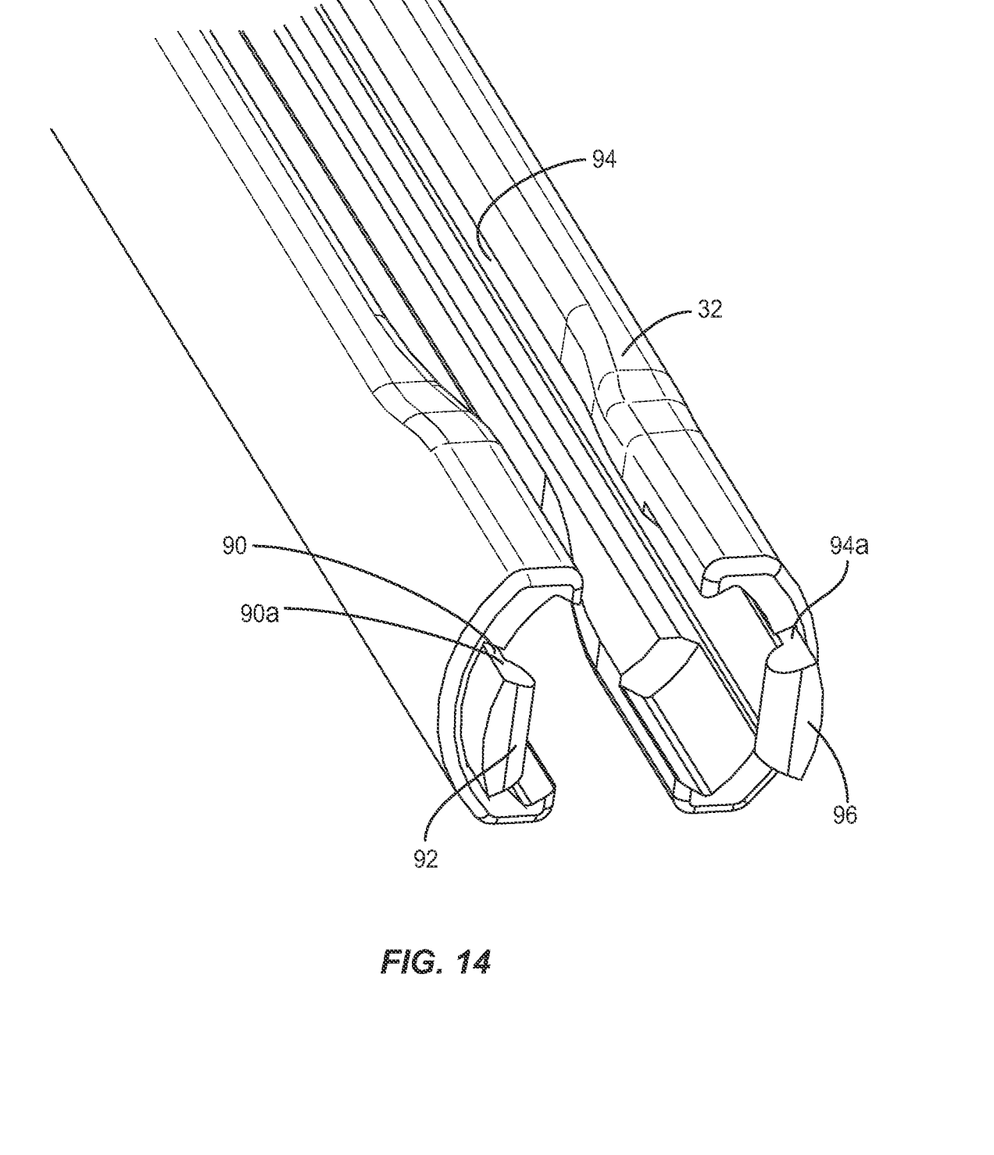
FIG. 14 is a break away perspective view of a distal end of the system shown in FIG. 1.

Referring to FIGS. 14-18, distal end 93 of extender 34 is inserted into keyway 65 of sleeve 32 such that the outer surfaces of first and second arms 90, 94 engage side surfaces 65a, 65b of keyway 65. First arm 90 is inserted into arcuate channel 114 such that the outer surface of first arm 90 engages side surface 65a and second arm 94 is inserted into arcuate channel 116 such that the outer surface of second arm 94 engages side surface 65b. Extender 34 is advanced axially toward distal end 62 of sleeve 32 such that first arm 90 is received within longitudinal channel 102 and second arm 94 is received within longitudinal channel 108, as shown in FIG. 14.

Figure 15:
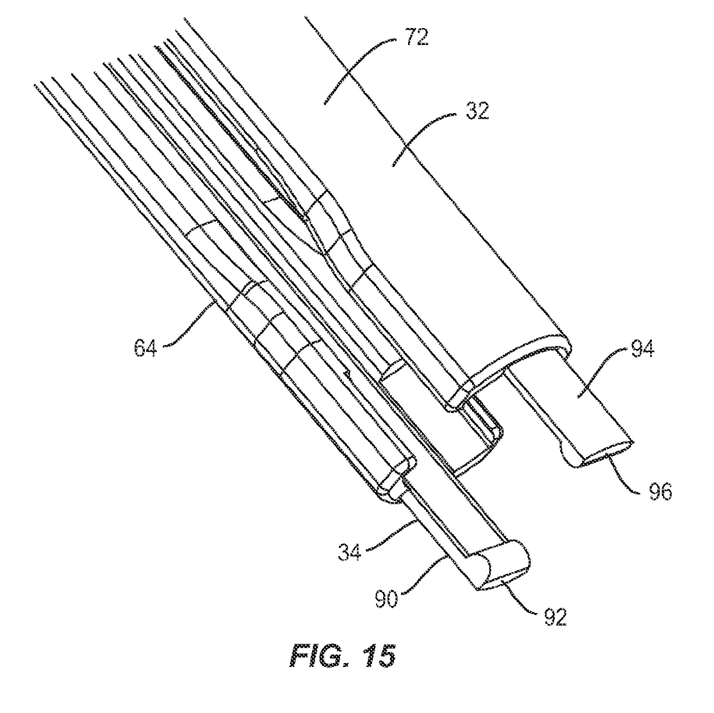
FIG. 15 is a break away perspective view of the distal end of the system shown in FIG. 1.
Figure 16:
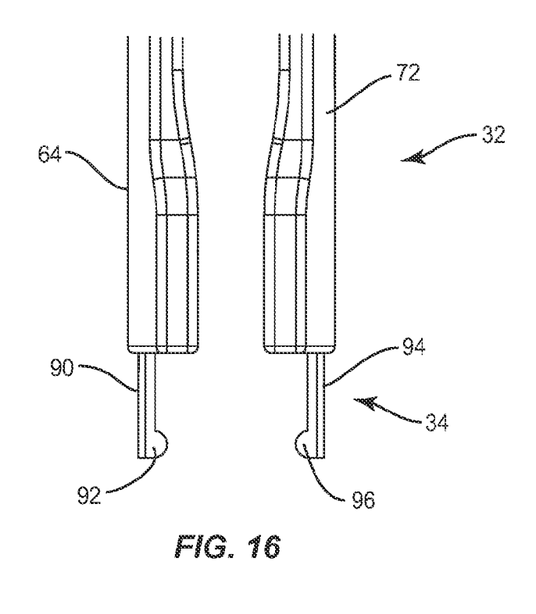
FIG. 16 is a break away side view of the distal end of the system shown in FIG. 1.

Extender 34 is advanced axially toward distal end 62 of sleeve 32. Proximal end 91 of extender 34 is received within channel 118 of sleeve 32. Extender 34 is advanced distally through distal end 62 of sleeve 32 with first arm 90 received within longitudinal channel 102 and second arm 94 received within longitudinal channel 108 such that the distal ends of first and second arms 90, 94 are distal to distal end 62 of sleeve 32, as shown in FIGS. 15-16. Extender 34 is assembled with sleeve 32 such that first and second arms 90, 94 are received within longitudinal channels 102, 108. Extender 34 is axially translatable relative to sleeve 32. In one embodiment, the spinal implant system includes a rotating nut mounted with sleeve 32 and/or extender 34 that rotates to drive the axial translation of extender 34 relative to sleeve 32.

The biasing member of the actuator described above, such as a spring, provides a bias such that extender 34 is biased to the second orientation, as shown in FIG. 14. A force is applied to proximal end 90 of extender 34 causing the spring to compress such that the distal ends of first and second arms 90, 94 may be axially advanced distally, as shown in FIGS. 15 and 16, to the first orientation in an unloaded state.

Figure 17:
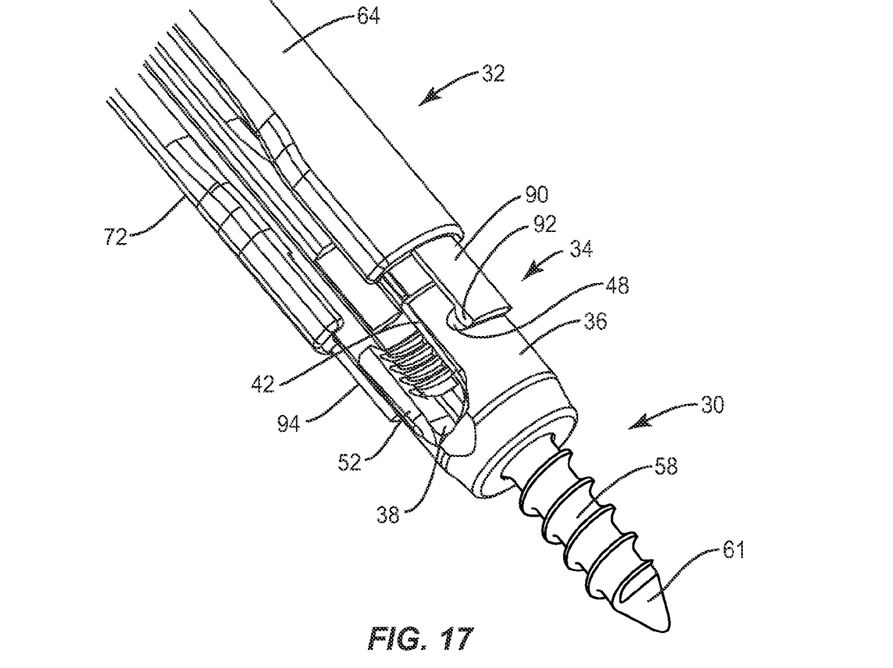
FIG. 17 is an enlarged perspective view of the distal end of the system shown in FIG. 1.
Figure 18:
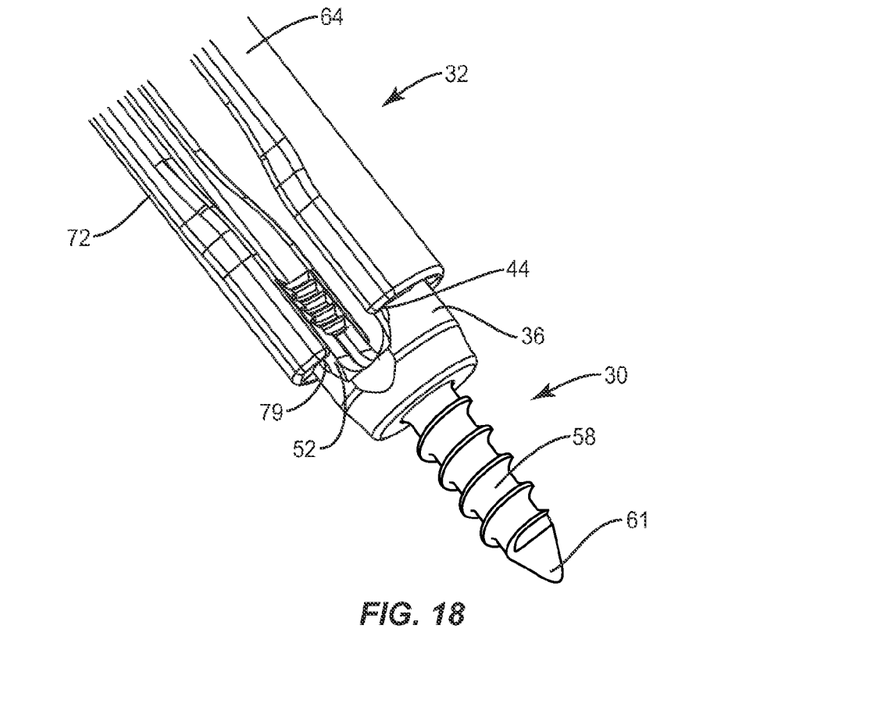
FIG. 18 is an enlarged perspective view of the distal end of the system shown in FIG. 1.

Bone fastener 30 is provisionally captured by extender 34, as shown in FIG. 17, such that transverse protrusions 92, 96 are received within transverse grooves 48, 56 of bone fastener 30. Proximal end 90 of extender 34 is released and the spring expands such that extender 34 axially translates relative to sleeve 32 with bone fastener 30 connected thereto being retracted proximally. At least a portion of bone fastener 30 is received within distal end 62 of sleeve 32, as shown in FIG. 18. Wall portions 36, 38 of bone fastener 30 are received within transverse channels 73, 81 of sleeve 32 such that first and second axial surfaces 42, 44, 50, 52 mate with faces 69, 71, 77, 79, and the spinal implant system is disposed in a loaded state. Pilot holes or the like are made in vertebrae (not shown) for receiving penetrating portion 58 of bone fastener 30. The spinal implant system is disposed adjacent the vertebrae at a surgical site and sleeve 32 is manipulable to drive, torque, insert or otherwise connect bone fastener 30 to vertebrae, according to the particular requirements of the surgical treatment.

Bone fastener 30 may be employed as a bone screw, pedicle screw, or multi-axial screw used in spinal surgery. It is contemplated that bone fastener 30 may be coated with an osteoconductive material such as hydroxyapatite and/or osteoinductive agent such as a bone morphogenic protein for enhanced bony fixation. Bone fastener 30 can be made of radiolucent materials such as polymers. Radiomarkers may be included for identification under x-ray, fluoroscopy, CT, or other imaging techniques. Metallic or ceramic radiomarkers, such as tantalum beads, tantalum pins, titanium pins, titanium endcaps, and platinum wires can be used.

It is envisioned that the spinal implant system may include one or a plurality of extenders, inserters, reducers, bone fasteners and/or vertebral constructs, which may be alternately sized and dimensioned, and arranged as a kit, according to the requirements of a particular application.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
   a first member extending along a longitudinal axis between a proximal portion and a distal portion, the proximal portion including a pair of walls, inner surfaces of the walls defining an implant cavity, the distal portion including a tissue penetrating portion, the walls each including first and second axial end surfaces that each extend from the inner surface of one of the walls to an opposite outer surface of one of the walls, the outer surfaces each including a locking cavity;
   a second member comprising a body and a pair of extensions that extend from the body, the extensions being spaced apart from one another by a first cavity, the extensions each comprising opposing faces that engage the axial end surfaces of one of the walls to couple the second member to the first member; and
   a third member disposed in the first cavity, and including an inner surface having a protrusion extending therefrom, wherein the third member is configured for axial translation relative to the second member between a first orientation in which the protrusion is disposed in one of the locking cavities and a second orientation in which the protrusion is spaced apart from the locking cavities.

2. The spinal implant system of claim 1, wherein the opposing faces define a longitudinal channel, the walls each being positioned within one of the longitudinal channels.

3. The spinal implant system of claim 1, wherein the tissue penetrating portion is rotationally fixed to the proximal portion.

4. The spinal implant system of claim 1, wherein the tissue penetrating portion is configured for multi-axial positioning with respect to the proximal portion.

5. The spinal implant system of claim 1, wherein the locking cavities each extend perpendicular to the longitudinal axis.

6. The spinal implant system of claim 1, wherein at least one of the locking cavities is a blind hole.

7. The spinal implant system of claim 1, wherein the first and second axial end surfaces of a respective one of the walls are positioned at opposite sides of the respective one of the walls.

8. The spinal implant system of claim 1, wherein the protrusion is biased inwardly toward the one of the locking cavities as the third member translates axially relative to the second member.

9. The spinal implant system of claim 1, wherein the first and second axial end surfaces of a respective one of the walls are each orientated at an acute angle relative to an outer circumference defined by the outer surface of the respective one of the walls.

10. The spinal implant system of claim 1, wherein the protrusion extends perpendicular to the inner surface of the third member.

11. The spinal implant system of claim 1, wherein the protrusion has an arcuate configuration.

12. The spinal implant system of claim 1, wherein the inner surface of the second member is concavely curved between the opposing faces and wherein the outer surfaces of the walls are each convexly curved between the first and second axial end surfaces.

13. The spinal implant system of claim 1, wherein the walls each include a proximal end surface extending perpendicular to the longitudinal axis, the first and second axial surfaces extending through the proximal end surfaces.

14. The spinal implant system of claim 1, wherein the protrusion occupies substantially all of the one of the locking cavities when the protrusion is received within the one of the locking cavities.

15. The spinal implant system of claim 1, wherein the locking cavities are each positioned between the axial surfaces of a respective one of the walls, the axial end surfaces each defining a thickness of one of the walls, wherein a distance between the axial end surfaces of the respective one of the walls defines a maximum width of the respective one of the walls.

16. A spinal implant system comprising:
   a bone fastener extending along a longitudinal axis between a proximal portion and a distal portion including a tissue penetrating portion, the proximal portion including opposing wall portions, inner surfaces of the wall portions defining an implant cavity, the wall portions each comprising first and second axial end surfaces that each extend from the inner surface of one of the walls to an opposite outer surface of one of the walls, the outer surfaces each including a transverse groove;
   a sleeve extending comprising a body and a pair of extensions that extend from the body, the extensions being spaced apart from one another by a first cavity, the extensions each comprising opposing faces that engage the axial end surfaces of one of the wall portions to couple the sleeve to the bone fastener; and
   an extender disposed in the first cavity, and including an inner surface including a transverse protrusion extending therefrom,
   wherein the extender is configured for axial translation relative to the sleeve between a first orientation in which the transverse protrusion is disposed in one of the transverse grooves and a second orientation in which the transverse protrusion is spaced apart from the transverse grooves.

17. The spinal implant system of claim 16, wherein the opposing faces define a longitudinal channel, the wall portions walls each being received within one of the longitudinal channels.

18. The spinal implant system of claim 16, further comprising a lock that prevents axial translation of the extender relative to the sleeve.

19. A method for treating a spine, the method comprising the steps of:
   providing a spinal implant system including:
      a first member extending along a longitudinal axis between a proximal portion and a distal portion, the proximal portion including a pair of walls, inner surfaces of the walls defining an implant cavity, the distal portion including a tissue penetrating portion, the walls each including first and second axial end surfaces that each extend from the inner surface of one of the walls to an opposite outer surface of one of the walls, the outer surfaces each including a locking cavity,
      a second member comprising a body and a pair of extensions that extend from the body, the extensions being spaced apart from one another by a first cavity, the extensions each comprising opposing faces that engage axial end surfaces of one of the walls to couple the second member to the first member, and
      a third member disposed in the first cavity, and including an inner surface having a protrusion extending therefrom;
   axially translating the third member relative to the second member to a first orientation such that the protrusion is disposed in one of the locking cavities; and
   axially translating the third member relative to the second member to a second orientation such that the protrusion is spaced apart from the locking cavities.

20. The spinal implant system of claim 19, further comprising the step of delivering the first member to a surgical site.

* * * * *

UNITED STATES PATENT AND TRADEMARK OFFICE
CERTIFICATE OF CORRECTION

PATENT NO. : 9,333,012 B2  
APPLICATION NO. : 13/280462  
DATED : May 10, 2016  
INVENTOR(S) : Beale et al.

Page 1 of 1

It is certified that error appears in the above-identified patent and that said Letters Patent is hereby corrected as shown below:

Specification

In Column 9, Line 43, delete "extender 32." and insert -- extender 34. --, therefor.

In Column 13, Line 31, delete "proximal end 90" and insert -- proximal end 91 --, therefor.

In Column 13, Line 38, delete "Proximal end 90" and insert -- Proximal end 91 --, therefor.

Signed and Sealed this  
Twenty-third Day of August, 2016

Michelle K. Lee  
*Director of the United States Patent and Trademark Office*